United States Patent
Beal (10) Patent No.: US 9,480,622 B1
(45) Date of Patent: Nov. 1, 2016

(54) MEDICAL DEVICE SAFETY HOLDER

(71) Applicant: Terry Beal, Copperas Cove, TX (US)

(72) Inventor: Terry Beal, Copperas Cove, TX (US)

(*) Notice: Subject to any disclaimer, the term of this patent is extended or adjusted under 35 U.S.C. 154(b) by 0 days.

(21) Appl. No.: 14/829,731

(22) Filed: Aug. 19, 2015

(51) Int. Cl.
*B25J 15/00* (2006.01)
*A61J 1/16* (2006.01)
*B01L 9/00* (2006.01)

(52) U.S. Cl.
CPC ... *A61J 1/16* (2013.01); *B01L 9/00* (2013.01)

(58) Field of Classification Search
CPC .......................................................... A61J 1/16
USPC ....... 294/34, 33, 57, 103.1, 901; 269/47, 89, 269/100; 248/207, 309.1, 309.2, 312, 313, 248/316.4
See application file for complete search history.

(56) References Cited

U.S. PATENT DOCUMENTS

| | | | | |
|---|---|---|---|---|
| 1,245,828 A * | 11/1917 | Cauwenbergh | ......... | B25B 5/006 269/100 |
| 1,714,555 A * | 5/1929 | Gallimore | ............... | B23Q 3/062 269/100 |
| 2,908,923 A * | 10/1959 | Schlechter | ........... | G02C 13/006 15/118 |
| 3,214,210 A * | 10/1965 | Keirn | ...................... | H01J 9/003 294/33 |
| 3,947,010 A * | 3/1976 | Zeller | ...................... | B62H 3/02 211/17 |
| 4,429,724 A * | 2/1984 | Dorros | ............... | A61M 25/1018 141/27 |
| 4,717,386 A * | 1/1988 | Simmons | ............ | A61M 5/3213 604/192 |
| 4,846,803 A * | 7/1989 | Emerson | ............. | A61M 5/3213 206/365 |
| 5,112,314 A * | 5/1992 | Aragon | ............... | A61M 5/3213 604/192 |
| 5,370,020 A * | 12/1994 | Fifield | ..................... | B25C 3/008 294/99.2 |
| 7,686,269 B1 * | 3/2010 | Beal | ......................... | A61J 1/16 248/104 |
| 2004/0004171 A1 * | 1/2004 | Beal | ......................... | A61J 1/16 248/313 |
| 2012/0000571 A1 * | 1/2012 | Foscarota | ................. | A61J 1/16 141/2 |

* cited by examiner

*Primary Examiner* — Paul T Chin
(74) *Attorney, Agent, or Firm* — Michael Diaz (57) ABSTRACT

The present invention provides a medical safety device for holding a container. The medical safety device is used to hold the container while extracting liquid by a syringe from the container. The medical safety device includes a main body having an opening for an interior. The interior has a retention space configured for retaining a container. In addition, the main body includes a plunger having a retention surface configured for contacting and retaining a container in the retention space. The plunger slides up and down within the retention space. Two handles are affixed to opposing sides of the main body. The plunger and retention surface applies force to the container positioned within the retention space sufficient to hold the container in place within the retention space. The plunger may be biased down into the retention space by a spring attached to the plunger.

17 Claims, 8 Drawing Sheets

MEDICAL DEVICE SAFETY HOLDER

BACKGROUND OF THE INVENTION

1. Field of the Invention

This invention relates to medical safety equipment. Specifically, and not by way of limitation, the present invention relates to a device for holding a container of medicinal or diagnostic agent.

2. Description of the Related Art

Healthcare workers are often required to dispense medication via a syringe from a vial or ampule. Typically, the healthcare worker is required to insert a needle of the syringe though a seal on the top portion of a vial, load the syringe with medication, and then inject the medication into the patient. However, there are two well-known safety hazards which are present during this procedure. One problem involves the risk of accidentally being stuck by a needle while loading a syringe, such as where a healthcare worker accidentally sticks himself or sticks another individual who is assisting in loading the syringe. This risk is particularly acute when one person holds the vial while the other person inserts the needle into the vial or when the syringe is loaded in a dimly lit room. Each year, hundreds of thousands of health care workers suffer from needle stick accidents. Obviously this is a dangerous situation where the healthcare worker is at risk for contracting many types of blood borne illnesses, such as hepatitis C virus (HCV), hepatitis B virus (HBV), human immunodeficiency virus (HIV) and other viral and bacterial diseases. Another problem occurs when a healthcare worker must load a syringe while working in a sterile environment. In such a situation, loading a syringe presents the risk of contaminating either the healthcare profession or the environment. For example, when a doctor is performing surgery in an operating room, touching an object that has not been sterilized, such as a vial, presents the risk of contamination through the operating field, and the spread of bacteria. To prevent contacting these unsterile objects, typically another individual must hold the vial while the physician loads the syringe. However, the assistance of another person obviously presents an additional risk of contamination, especially when that person's hands come into close proximity to the syringe being loaded. Thus, there is a need for a device that can be sterilized and allows a doctor or other healthcare worker to load a syringe in a sterile environment without the aid of a second individual or allows the second individual to keep his hands away from the syringe.

Additionally, although there are no known prior art teachings of a device such as that disclosed herein, prior art references that discuss subject matter that bears some relation to matters discussed herein are U.S. Pat. No. 7,686,269 to Beal (Beal), U.S. Pat. No. 2,908,923 to Schlechter (Schlechter), U.S. Pat. No. 3,214,210 to Keirn (Keirn), and U.S. Pat. No. 5,370,020 to Fifield et al. (Fifield).

Beal discloses a device which includes a slit having two interior walls which are biased toward each other. A container may be placed within the slit and held stationary within the slit by force being directed to the side walls of the container. However, Beal does not disclose a plunger mechanism for holding the container in place. Rather, Beal utilizes two interior walls of the single unitary device to hold the container in place.

Schlechter discloses a lens cleaning device having a body with a handle and an outwardly extending U-shaped arm. The arm includes a lens cleaning element mounted to the U-shaped arm. Although this device is non-analogous art, the device does disclose a U-shaped arm which may be squeezed together to retain an object, namely a lens. However, Schlechter suffers from the disadvantage of requiring pressure to be applied by the user to retain the object. Schlechter also does not disclose retaining a vial or any object within the U-shaped arm.

Keirn discloses a device to remove electronic tubes which includes a handle having a U-shape and a pair of parallel elongated arms which are hinged. However, Keirn requires the user to hold both arms together to retain an object.

Fifield discloses a nail holder having a resilient plastic handle formed in a U-shape and a pair of parallel arms. The device is hinged and may be squeezed together to grip an object. Fifield also requires the user to actively squeeze the arms together to hold the nail.

Schlechter, Keirn and Fifield do not provide separate handles for holding the holding device. Without two handles to hold the holding device, holding it is very cumbersome to the user. In regards to Beal, Beal does not use a separate retention mechanism and relies on the bias of the two sides of a slit to hold the container. Thus, it would be a distinct advantage to have an apparatus which is easy to hold and provides a secure way of holding the container within the safety device. It is an object of the present invention to provide such an apparatus.

SUMMARY OF THE INVENTION

In one aspect, the present invention is a medical safety device for retaining a container. The medical safety device includes a main body having an opening for an interior. The interior has a retention space configured for retaining a container. In addition, the main body includes a plunger having a retention surface configured for contacting and retaining a container in the retention space. The plunger slides up and down within the retention space. Two handles are affixed to opposing sides of the main body. The plunger and retention surface applies force to the container positioned within the retention space sufficient to hold the container in place within the retention space. The plunger may be biased down into the retention space by a spring attached to the plunger.

In another aspect, the present invention is a medical safety device for holding a container while a syringe extracts liquid from the container. The medical safety device includes a main body having an opening for an interior, the interior having a retention space configured for retaining a container. Additionally, the main body includes a plunger having a retention surface configured for contacting and retaining a container in the retention space. Two handles are affixed to opposing sides of the main body. The plunger and retention surface applies force to the container positioned within the retention space sufficient to hold the container in place within the retention space while a syringe extracts liquid from the container.

DESCRIPTION OF THE INVENTION

Figure 1:
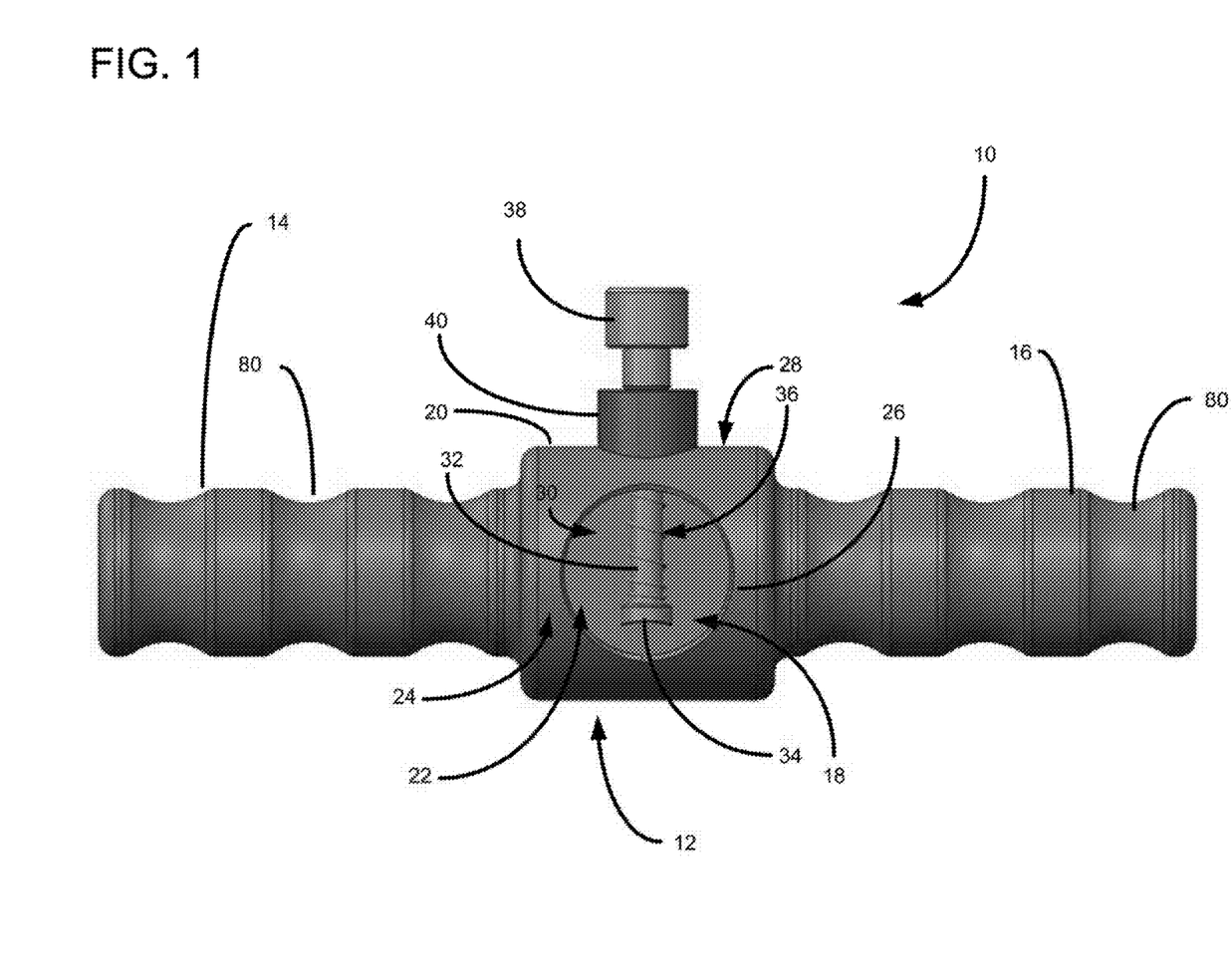
FIG. 1 is a front perspective view of a safety device in a home position in one embodiment of the present invention.

The present invention is a safety device for holding a container holding a medicinal or diagnostic agent. FIG. 1 is a front perspective view of a safety device 10 in a home position in one embodiment of the present invention. The safety device includes a main body 12 having two opposing handles 14 and 16. The main body also includes an interior 18 having a plurality of walls 20 forming a retention space 22. One side 24 of the main body 12 has an opening 26 sized to allow placement of a vial or container (not shown in FIG. 1). On a side 28 perpendicular and adjacent to the side 24 is positioned a plunger 30. The plunger 30 includes a retention rod 32 with a retention surface 34, a spring 36, and an exterior handhold 38. The plunger is biased to the home position depicted in FIG. 1 with the spring pushing down on the retention rod 32 and the retention surface 34. A portion of the retention rod 32 and the entire retention surface 34 resides in the retention space 22. The plunger is held in place at a collar 40 located on an exterior surface of the side 28.

Figure 2:
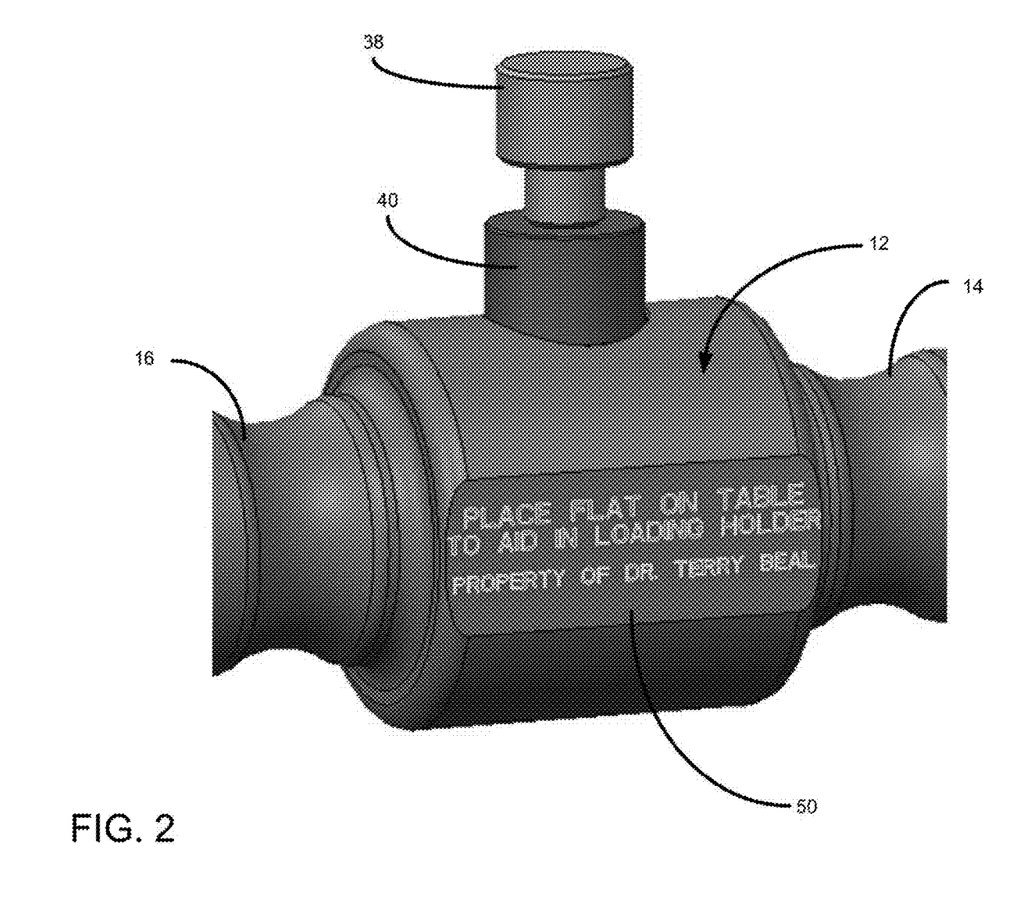
FIG. 2 is a rear view of the main body of the safety device of FIG. 1.

FIG. 2 is a rear view of the main body 12 of the safety device 10 of FIG. 1. The main body may have a flat portion 50 located on a least one side of the main body. The flat portion may be positioned on top of another stable flat surface, such as a table and used to facilitate the loading of a vial or container into the safety device 10. As shown in FIG. 2, the flat portion 50 of the main body 12 is located on an opposite side from the opening 26.

Figure 3:
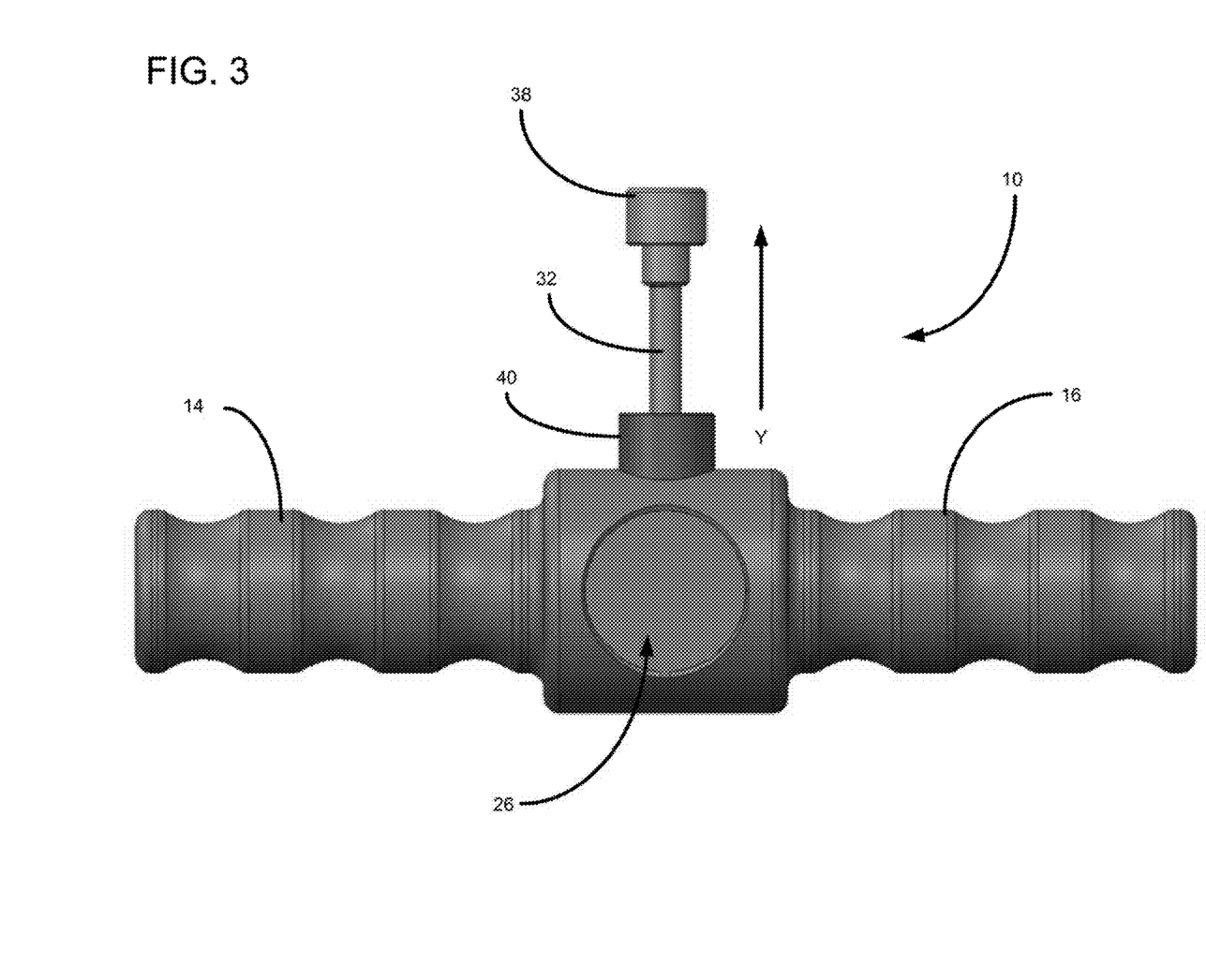
FIG. 3 is a front perspective view of the safety device with the plunger lifted to a receiving position to allow positioning of a vial in the retention space.

FIG. 3 is a front perspective view of the safety device 10 with the plunger lifted to a receiving position to allow positioning of a vial in the retention space 22. The plunger is constructed in such a fashion as to allow movement of the plunger along the Y axis when a user pulls up on the exterior handhold 38, thereby moving the retention surface 34 upward.

Figure 4:
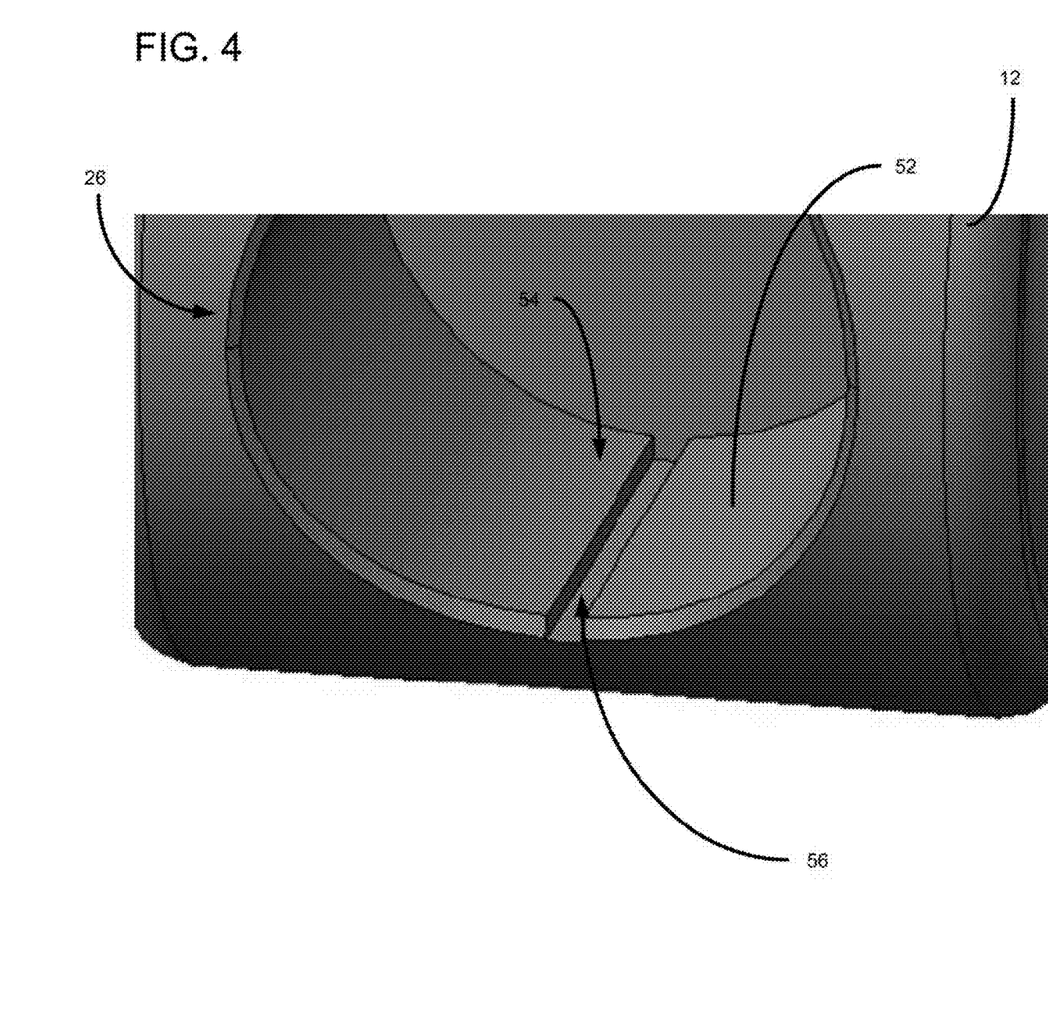
FIG. 4 is an enlarged front view of the retention space.

FIG. 4 is an enlarged front view of the retention space 22. The retention space 22 may include a curved interior wall 52. As depicted in FIG. 1, the opening 26 as well as the retention space 22 may be circular in shaped. At a bottom portion 54 of the retention space 22 may be a linear groove 56. This linear groove may be utilized with smaller vials to allow two contact points for the vial, thereby preventing excessive movement of the vial retained by the retention surface 34.

Figure 5:
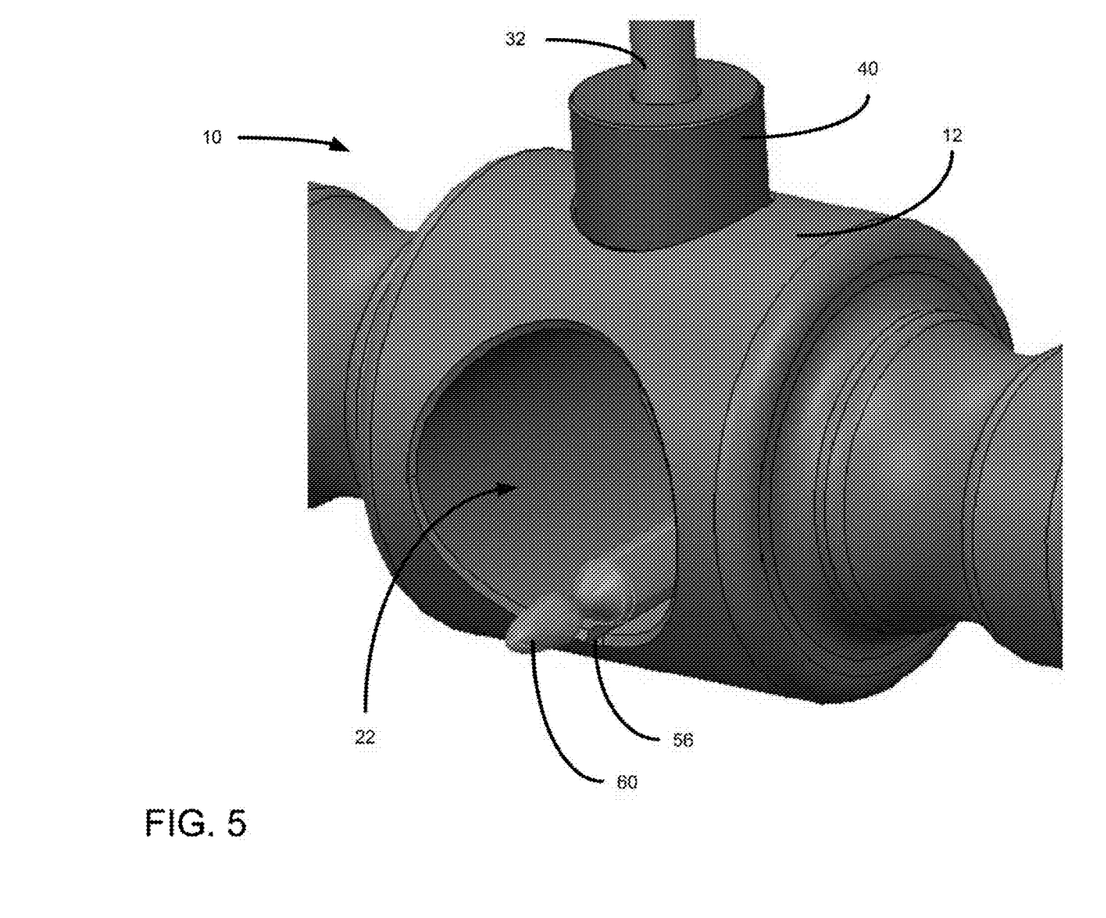
FIG. 5 is a front perspective view of the safety device with a vial positioned in the retention space.

FIG. 5 is a front perspective view of the safety device 10 with a vial 60 positioned in the retention space 22. The user raises the plunger 30 upward by pulling the exterior handhold 38 upwardly. The vial 60 may then be positioned in the retention space 22. As depicted in FIG. 5, the vial is positioned over the linear groove 56.

Figure 6:
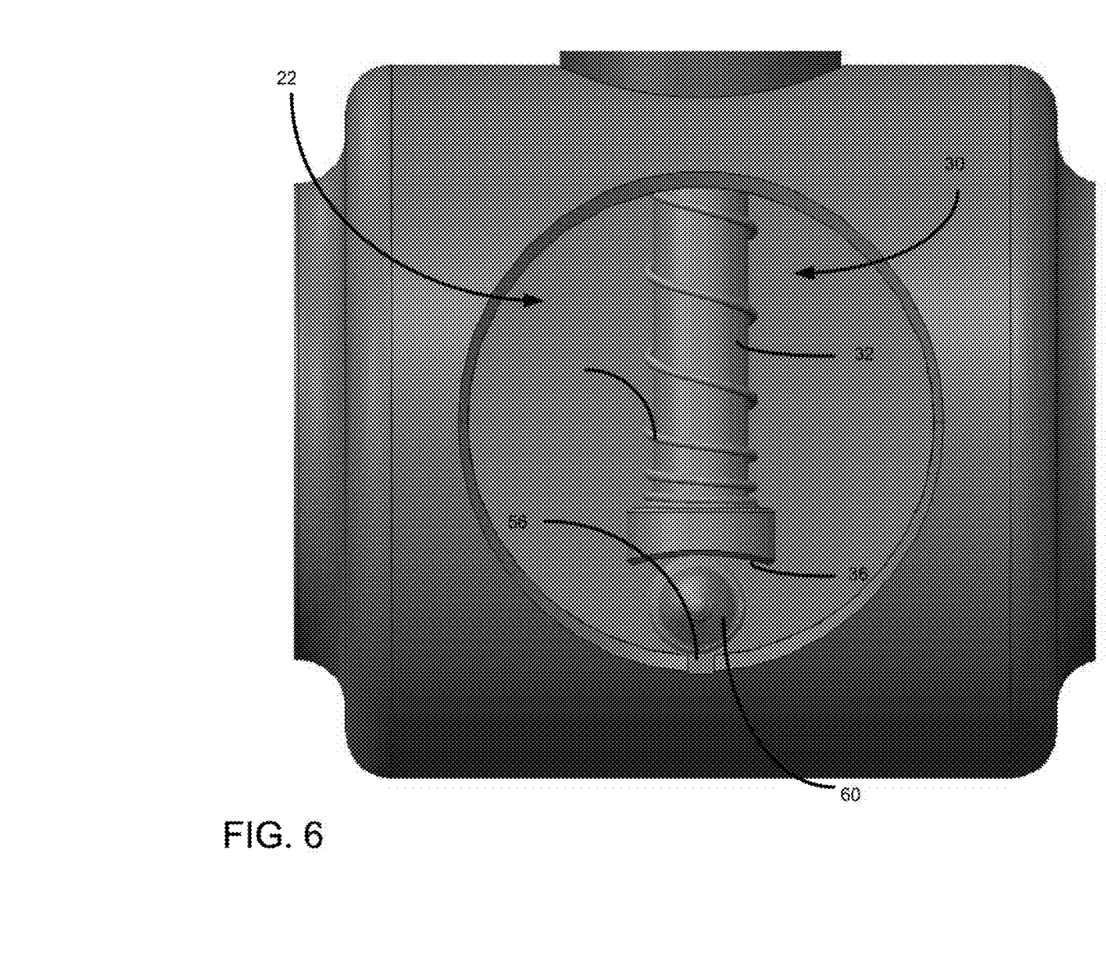
FIG. 6 is an enlarged front view of the vial held in place by the plunger in one embodiment of the present invention.

FIG. 6 is an enlarged front view of the vial 60 held in place by the plunger 30 in one embodiment of the present invention. After the vial 60 is positioned in the retention space 22, the exterior handheld 38 may be released by the user. The spring 36 biases the plunger downward, causing the retention surface 34 to apply a force to hold the vial in place in the retention space 22. Once the vial is held in place, a user may then perform actions on the vial, such as sticking a syringe into the vial. In one embodiment, the user grasps the handles 14 and 16 and positions the safety device 10 with its flat portion 50 against a flat surface.

Figure 7:
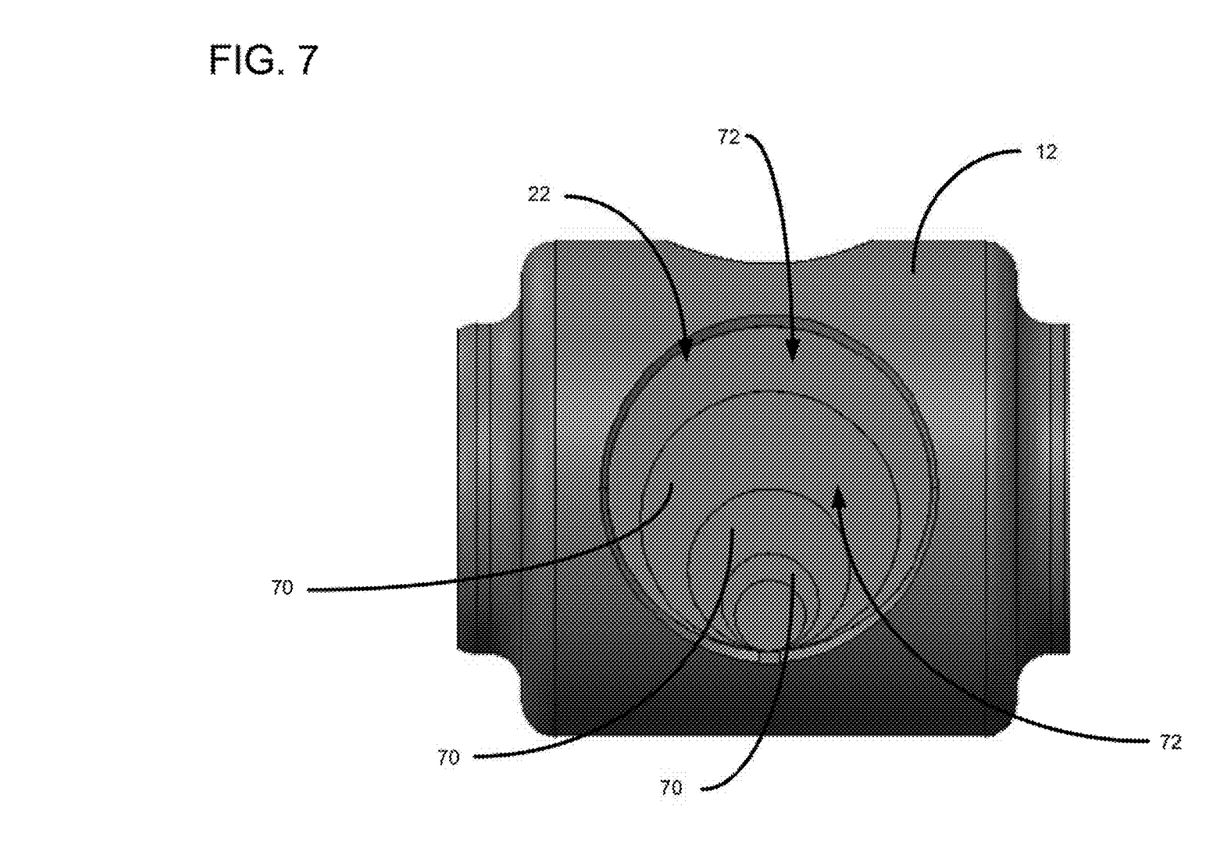
FIG. 7 is a front view of the retention space and plurality of bores.
Figure 8:
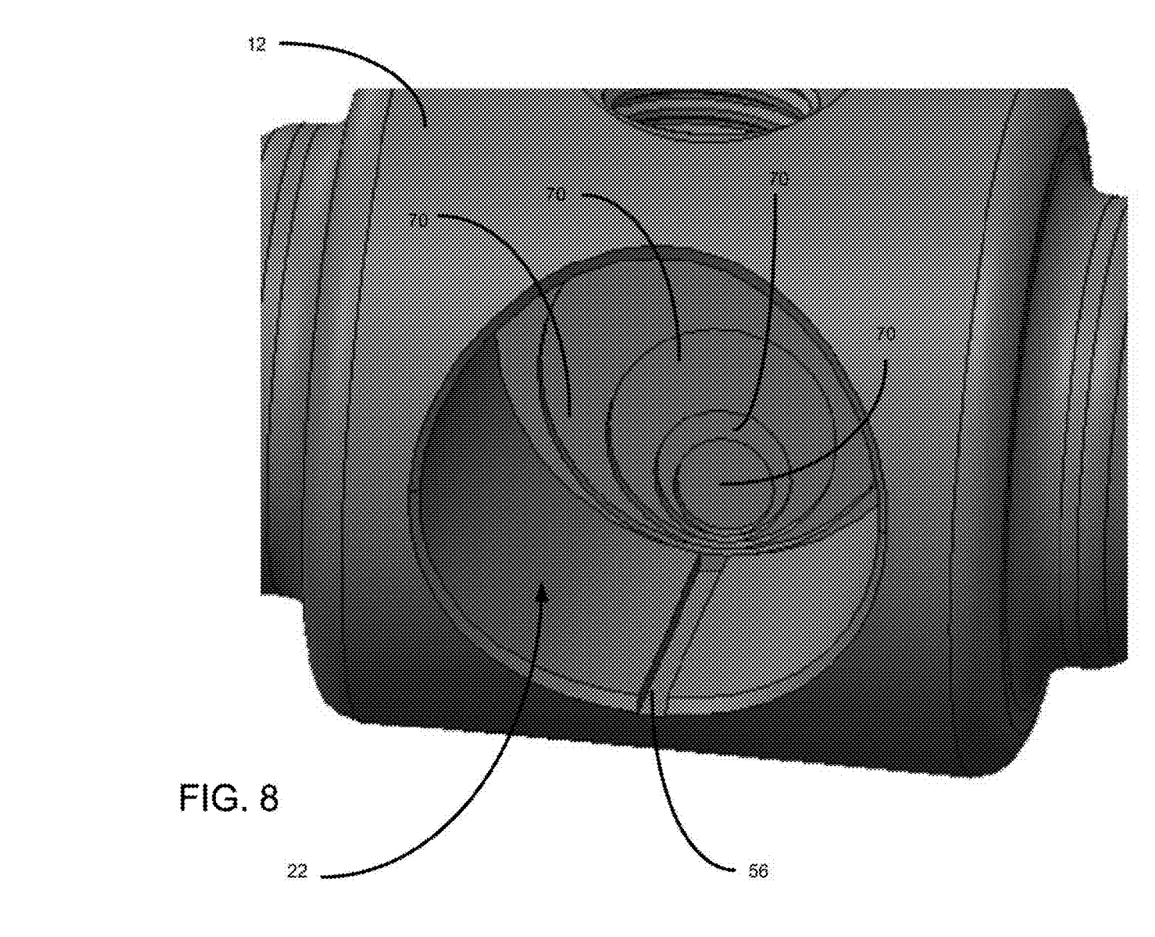
FIG. 8 is a second front view of the retention space of FIG. 7.

In one embodiment, a plurality of bores 70 may be formed at various depths in the retention space 22. The bores may be sized with varying diameters and shaped to fit various sizes of vials. In one embodiment, the bores may be sized to fit standardized sizes of vials or containers. FIG. 7 is a front view of the retention space 22 and plurality of bores 70. FIG. 8 is a second front view of the retention space of FIG. 7. The bores have curved walls 72 for retaining the vials within the retention space 22.

With reference to FIGS. 1-8, the operation of the safety device 10 will now be explained. The user moves the plunger up along the Y axis by pulling upward on the exterior handhold 38 of the plunger 30. By pulling up on the handhold 38, the retention rod 32 raises the retention surface 34 upward, allowing sufficient room for the vial 60 to be positioned within the retention space 22. The user then places the vial 60 in the retention space 22, preferably upon the linear groove 56 with the top of the vial pointing out toward the opening 26. The user then may gently lower or release the handhold 38. The spring biases the plunger to the home or lowered position (see FIGS. 1 and 6). The lowered plunger applies a force through the retention surface 34 upon the vial, thereby keeping the vial in place in the retention space. The user may then grasp one or both handles and stick a syringe in the top portion of the vial or allow another individual to stick a syringe in the vial while the user holds the safety device 10. During any operation upon the vial, the flat portion may be positioned on top of another stable flat surface, such as a table and used to facilitate the loading of a vial or container into the safety device 10. Since the user is holding the handles at a distance away from the vial, the risk of being stuck by a needle is reduced. Additionally, since the user does not need to perform any action to hold the vial in place, the user may use hold the safety device by one handle when performing any action on the vial. When the user is finished using the vial, the user may raise the exterior handhold 38 and remove the vial.

The safety device 10 is preferably constructed of a strong material which may be coated with a material to allow easy sterilization without damage to the safety device. In addition, in one embodiment of the present invention, the handles may include indentations or knurls 80 to assist in the gripping the handles 14 and 16 of the safety device 10. The present invention may be utilized on any container capable of being positioned within the retention space 22, such as a vial or ampule.

The present invention provides many advantages over existing retaining safety devices. The safety device enables a user to hold a container having a medicinal or diagnostic agent without actually touching the object. Thus, sterilization procedures common in the medical field may be maintained. The safety device may be sterilized and used in a sterile environment, which is critical in the medical field. Additionally, since a user is holding the vial by grasping one or both of the handles, the user's risk of being stuck by a needle is reduced because the user's hands are located a safe distance away from the vial.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

Thus, the present invention has been described herein with reference to a particular embodiment for a particular application. Those having ordinary skill in the art and access to the present teachings will recognize additional modifications, applications and embodiments within the scope thereof.

It is therefore intended by the appended claims to cover any and all such applications, modifications and embodiments within the scope of the present invention.

What is claimed is:

1. A medical safety device for retaining a medical container, the medical safety device comprising:
    a main body having an opening for an interior, the interior having a retention space configured for retaining a container;
    a plunger having a retention surface configured for contacting and retaining a container in the retention space;
    a first handle affixed to a first side of the main body;
    a second handle affixed to a second side of the main body opposite the first handle;
    wherein the plunger is positioned in an orientation perpendicular to the first and second handles;
    wherein the plunger is affixed to a retention rod having a spring, the spring configured to bias the plunger down into the retention space;
    wherein the first handle and second handle extend straight outwardly from the main body and are each configured for grasping by a hand of a user to hold the main body steady;
    wherein the medical safety device is configured to be held in position by the user by holding the first and second handles and remain unattached to a fixed object when retaining the container within the retention space;
    wherein the medical safety device is configured for use on medical containers;
    whereby the plunger and retention surface applies force to the container positioned within the retention space sufficient to hold the container in place within the retention space.

2. The medical safety device according to claim 1 wherein the retention rod having the retention surface affixed to a first end of the retention rod, the retention rod sliding within the retention space.

3. The medical safety device according to claim 2 wherein the plunger is attached to the main body at a collar affixed to an outer surface of the main body of the safety device.

4. The medical safety device according to claim 2 wherein the retention rod includes an exterior handhold affixed to a second end of the retention rod opposite the first end, the exterior handhold positioned outside the main body and configured for pulling by a user to raise the plunger.

5. The medical safety device according to claim 1 wherein the retention space includes a curved interior wall.

6. The medical safety device according to claim 5 wherein the curved wall includes a linear groove located at a lower portion of the curved wall, the linear groove adapted for holding the container.

7. The medical safety device according to claim 5 wherein the retention space includes a plurality of bores having diameters of varying sizes, each bore sized and shaped to accommodate a vial of a different diameter.

8. The medical safety device according to claim 1 wherein the first and second handles have indentation for gripping.

9. The medical safety device according to claim 1 wherein the main body includes a flat portion configured for placement of the medical safety device upon a flat surface.

10. The medical safety device according to claim 1 wherein the medical safety device is suitable for a sterile environment.

11. A medical safety device for holding a container while a syringe extracts liquid from the container, the medical safety device comprising:
    a main body having an opening for an interior, the interior having a retention space configured for retaining a container;
    a plunger having a retention surface configured for contacting and retaining a container in the retention space;
    a first handle affixed to a first side of the main body;
    a second handle affixed to a second side of the main body opposite the first handle;
    wherein the plunger is positioned in an orientation perpendicular to the first and second handles;
    wherein the plunger is affixed to a retention rod having a spring, the spring configured to bias the plunger down into the retention space;
    wherein the first handle and second handle extend straight outwardly from the main body and are each configured for grasping by a hand of a user to hold the main body steady;
    wherein the medical safety device is configured to be held in position by the user by holding the first and second handles and remain unattached to a fixed object when retaining the container within the retention space;
    wherein the medical safety device is configured for use on medical containers;
    whereby the plunger and retention surface applies force to the container positioned within the retention space sufficient to hold the container in place within the retention space while a syringe extracts liquid from the container.

12. The medical safety device according to claim 11 wherein the retention rod having the retention surface affixed to a first end of the retention rod, the retention rod sliding within the retention space.

13. The medical safety device according to claim 12 wherein the retention rod includes an exterior handhold affixed to a second end of the retention rod opposite the first end, the exterior handhold positioned outside the main body and configured for pulling by a user to raise the plunger.

14. The medical safety device according to claim 11 wherein the retention space includes a curved interior wall having a linear groove located at a lower portion of the curved wall, the linear groove adapted for holding the container.

15. The medical safety device according to claim 14 wherein the retention space includes a plurality of bores having diameters of varying sizes, each bore sized and shaped to accommodate a vial of a different diameter.

16. The medical safety device according to claim 11 wherein the first and second handles have indentation for gripping.

17. The medical safety device according to claim 11 wherein the main body includes a flat portion configured for placement of the medical safety device upon a flat surface.

* * * * *